(12) United States Patent
Yoon et al.

(10) Patent No.: US 8,608,314 B2
(45) Date of Patent: Dec. 17, 2013

(54) SCANNING OPTICAL SYSTEM FOR LARGE AXIAL SCAN DEPTH ANTERIOR SEGMENT OPTICAL COHERENCE TOMOGRAPHY (OCT)

(75) Inventors: Geunyoung Yoon, Pittsford, NY (US); Rahul Yadav, Rochester, NY (US)

(73) Assignee: University of Rochester, Rochester, NY (US)

( * ) Notice: Subject to any disclaimer, the term of this patent is extended or adjusted under 35 U.S.C. 154(b) by 88 days.

(21) Appl. No.: 13/295,824

(22) Filed: Nov. 14, 2011

(65) Prior Publication Data

US 2012/0127431 A1 May 24, 2012

Related U.S. Application Data

(60) Provisional application No. 61/414,088, filed on Nov. 16, 2010.

(51) Int. Cl.
*A61B 3/10* (2006.01)
*A61B 3/00* (2006.01)

(52) U.S. Cl.
USPC .......................................... 351/221; 351/246

(58) Field of Classification Search
USPC ................................................... 351/200–246
See application file for complete search history.

(56) References Cited

U.S. PATENT DOCUMENTS

| 8,049,873 B2 * | 11/2011 | Hauger et al. | 356/73 |
| 2009/0168017 A1 * | 7/2009 | O'Hara et al. | 351/205 |
| 2010/0091243 A1 * | 4/2010 | Bor | 351/219 |

OTHER PUBLICATIONS

Yadav, et al., "Scanning system Design for Large Scan Depth Anterior Segment Optical Coherence Tomography", The Institute of Optics, University of Rochester, Rochester, New York; Optics Letters/vol. 35, No. 11/Jun. 1, 2010 (3 pgs).

* cited by examiner

*Primary Examiner* — Mohammed Hasan
(74) *Attorney, Agent, or Firm* — Blank Rome LLP (57) ABSTRACT

An optical coherence tomography scanning system includes a lens divided into two halves: one optimized to achieve normal incidence angles on the posterior surface of the eye's lens, the other optimized for the anterior surface of the eye's lens.

13 Claims, 14 Drawing Sheets

Telecentric scan
First surface without distortion

Asymmetric scan
First surface distorted

SCANNING OPTICAL SYSTEM FOR LARGE AXIAL SCAN DEPTH ANTERIOR SEGMENT OPTICAL COHERENCE TOMOGRAPHY (OCT)

REFERENCE TO RELATED APPLICATION

The present application claims the benefit of U.S. Provisional Patent Application No. 61/414,088, filed Nov. 16, 2010, whose disclosure is hereby incorporated by reference in its entirety into the present disclosure.

FIELD OF THE INVENTION

The present invention is directed to a scanning optical system and more particularly to such a system having asymmetric focusing optics.

DESCRIPTION OF RELATED ART

Figure 1A:
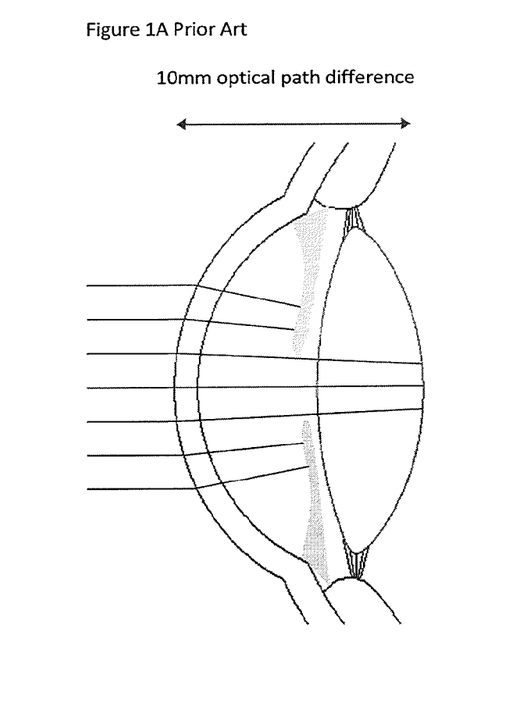
FIGS. 1A and 1B are a diagram and a photograph that show drawbacks of present optical coherence tomography.
Figure 1B:
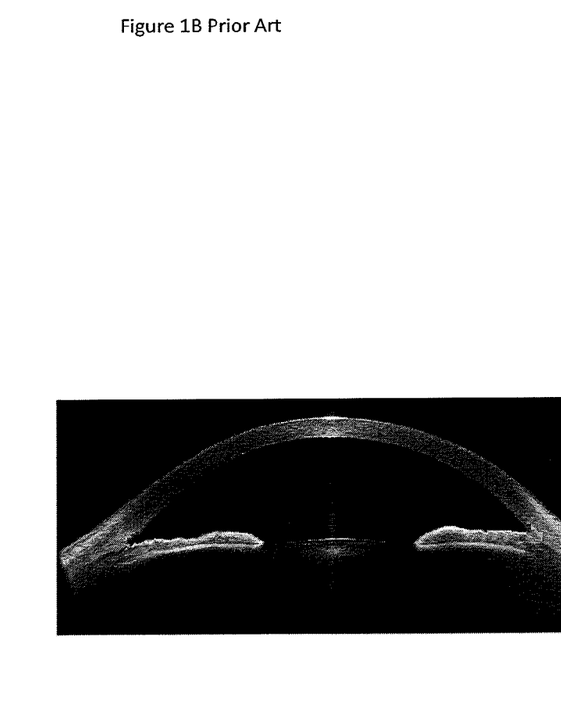

Large-scan-depth anterior segment OCT is important in understanding accommodation to measure the following: lens shape change with accommodation, age-related optical changes in the lens, and the efficacy of accommodative intraocular lenses (IOLs). However, the limitations of current anterior segment OCTs include a limited depth penetration, as shown in FIG. 1A and the need for pupil dilation, as shown in FIG. 1B.

More specifically, the total axial length of the anterior segment from the apex of the anterior cornea to the back surface of the lens is approximately 7.7 mm (10.2 mm optical path length at n=1.33). That poses a challenge, since sensitivity of an OCT system decreases with depth. Thus, the signal from the deeper ocular surfaces, especially the posterior surface of the lens, becomes weak. Most of the commercial anterior segment OCT systems use telecentric scan geometry in which the beam is shined straight into the eye parallel to the optical axis. The angle of incidence on the ocular surfaces, and especially the posterior surface of the crystalline lens, increases as the regions farther away from the optical axis of the eye are scanned. That leads to a significant reduction in the amount of backscattered light collected by the OCT system. The other limitation with traditional telecentric scan is the fact that pupil dilation is necessary to image a large diameter of the lens. The pupil dilation may cause some differences in accommodative response from naturally stimulated accommodation in which pupil size actually decreases with accommodation (known as pupil miosis).

SUMMARY OF THE INVENTION

It is therefore an object of the invention to overcome those limitations.

To achieve the above and other objects, the present invention is directed to an asymmetric focusing optics system which provides an angle of incidence of each scan beam normal to the ocular surfaces. That system includes a lens divided into two halves: one optimized to achieve normal incidence angles on the posterior surface of the lens, the other optimized for the anterior surface of the lens. Two semicircular halves from each system were glued together to form a single optical system. That configuration results in a substantial increase in light intensity reflected from each surface.

The inventor's work is described in Yadav et al, "Scanning system design for large scan depth anterior segment optical coherence tomography," *Optics Letters*, Vol. 35, no. 11, Jun. 1, 2010, whose disclosure is hereby incorporated by reference in its entirety into the present disclosure.

BRIEF DESCRIPTION OF THE DRAWINGS

A preferred embodiment of the present invention will be set forth in detail with reference to the drawings, in which:

FIGS. 3A-3D and 3F are drawings.

DETAILED DESCRIPTION OF THE PREFERRED EMBODIMENT

A preferred embodiment of the present invention will be set forth in detail with reference to the drawings, in which like reference numerals refer to like elements throughout.

Figure 2A:
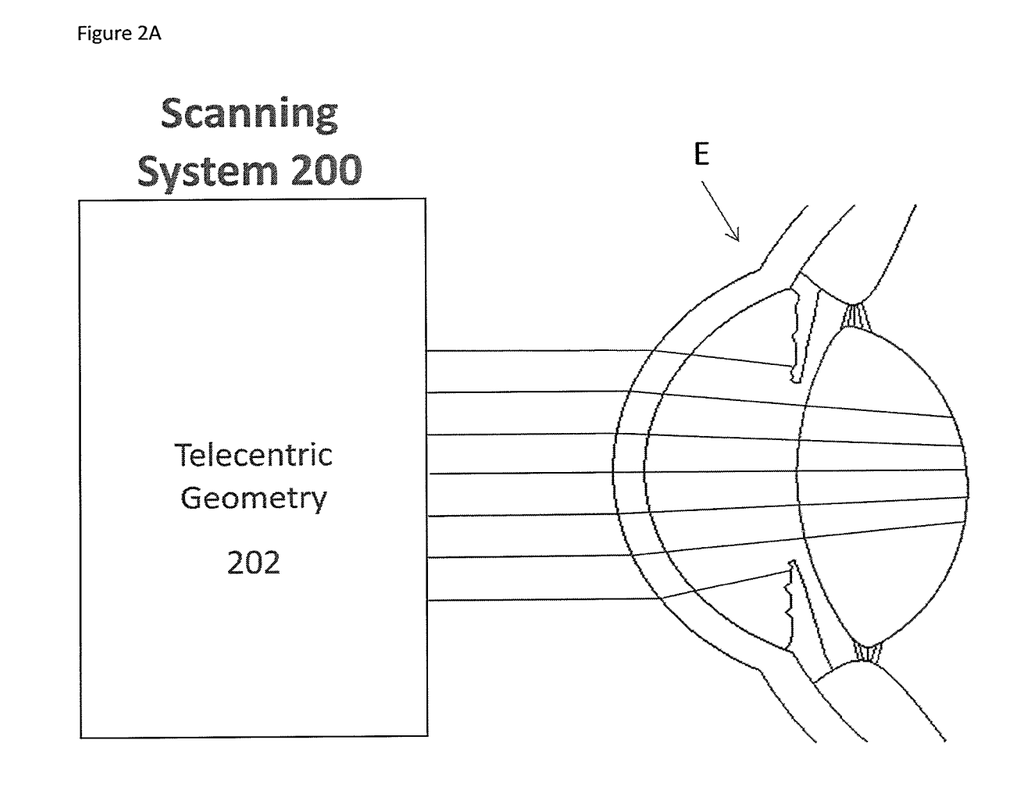
FIGS. 2A-2C are diagrams that show a first design principle of the present invention.
Figure 2B:
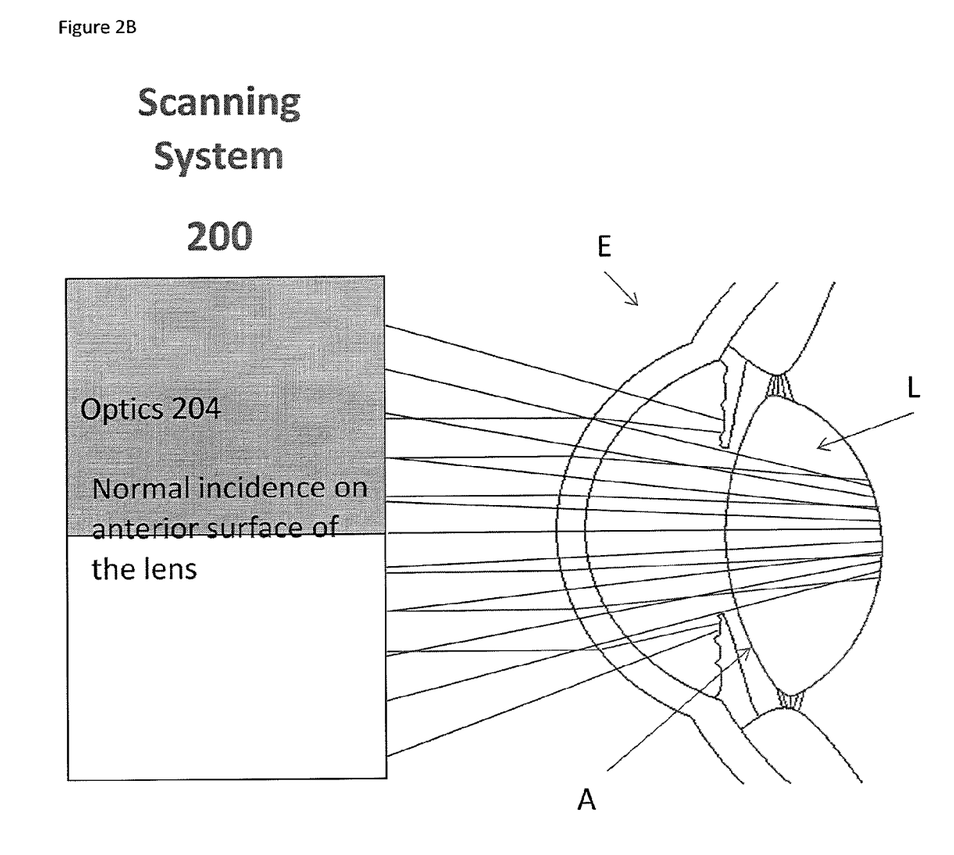
Figure 2C:
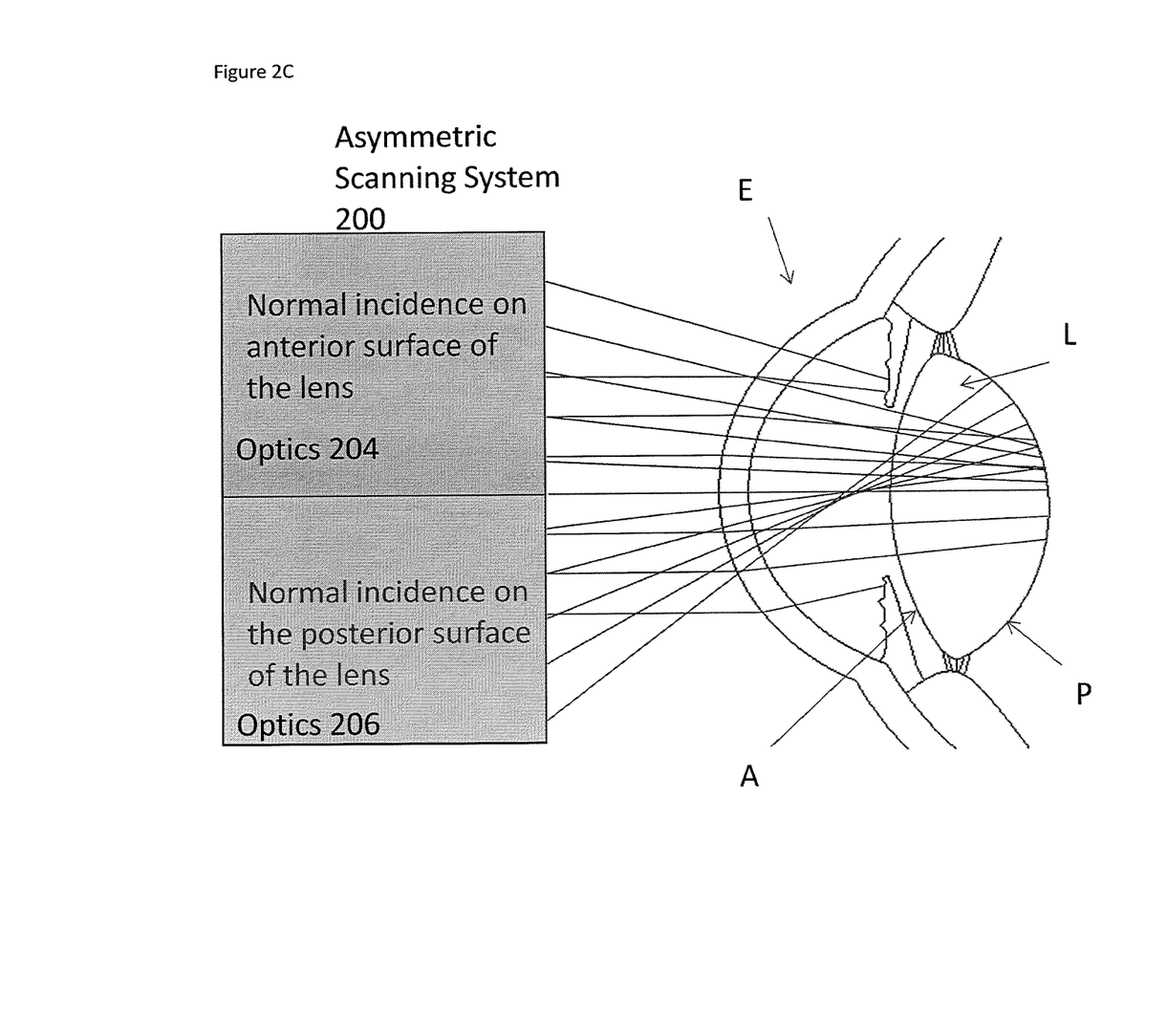

The first design principle will be described with reference to FIGS. 2A-2C. The scanning system 200 includes telecentric optics 202 configured for normal incidence on the ocular surfaces of the eye E. The telecentric optics 202 include optics 204 configured for normal incidence on the anterior surface A of the lens L, as shown in FIG. 2B, and optics 206 configured for normal incidence on the posterior surface P of the lens L, as shown in FIG. 2C. Thus, the scanning system 200 is asymmetric.

Figure 3A:
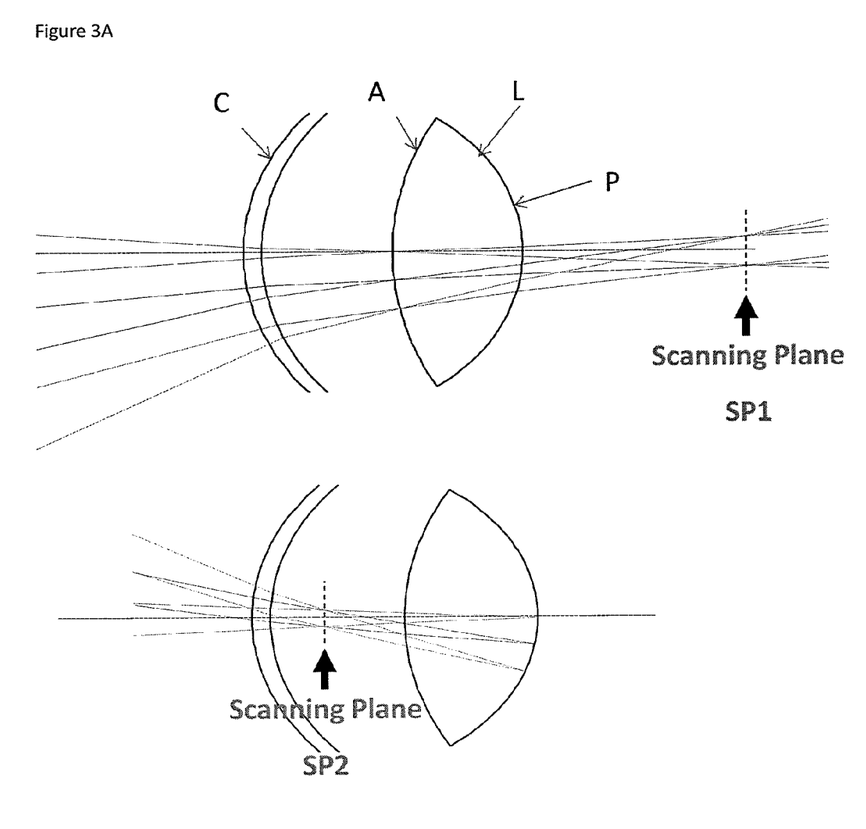

The second design principle will be described with reference to FIGS. 3A-3D. As shown in FIG. 3A, when the scanning light is made normally incident on the anterior surface A of the lens L, the scanning plane is a first scanning plane SP1 behind the lens. However, when the scanning light is made normally incident on the posterior surface P of the lens L, the scanning plane is a second scanning plane SP2 between the cornea C and the lens L.

Figure 3B:
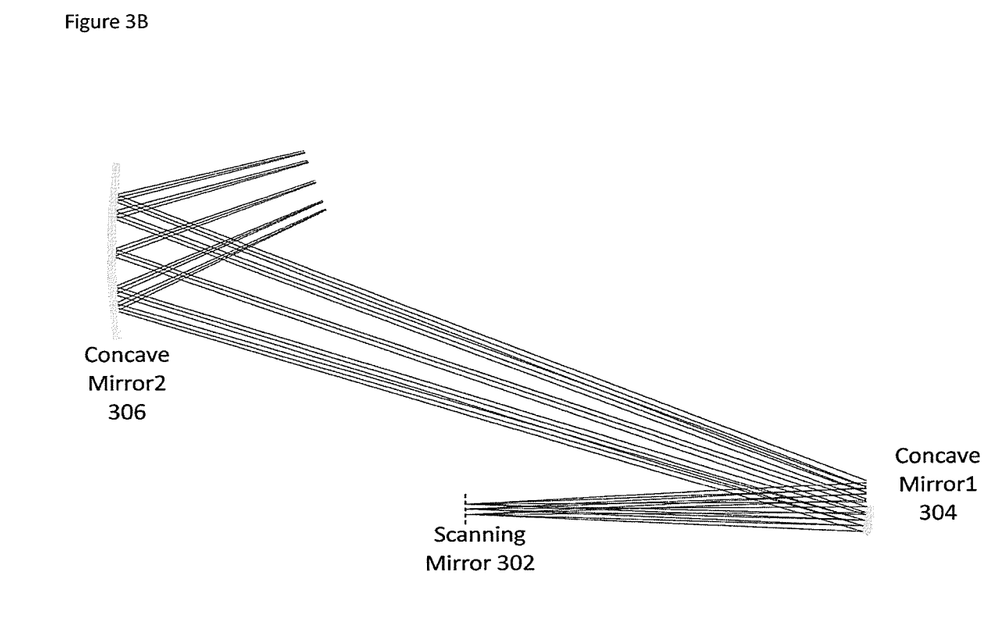
Figure 3C:
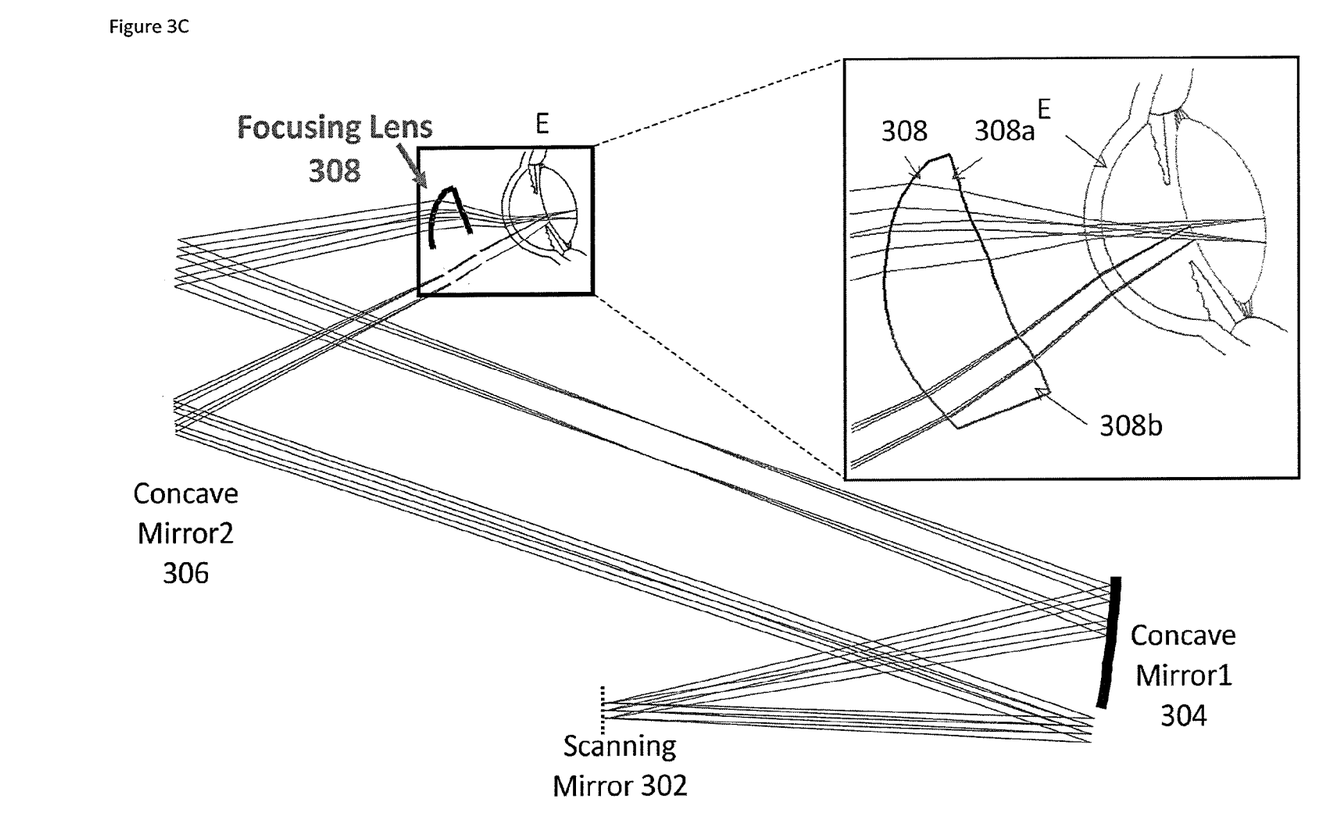
Figure 3D:
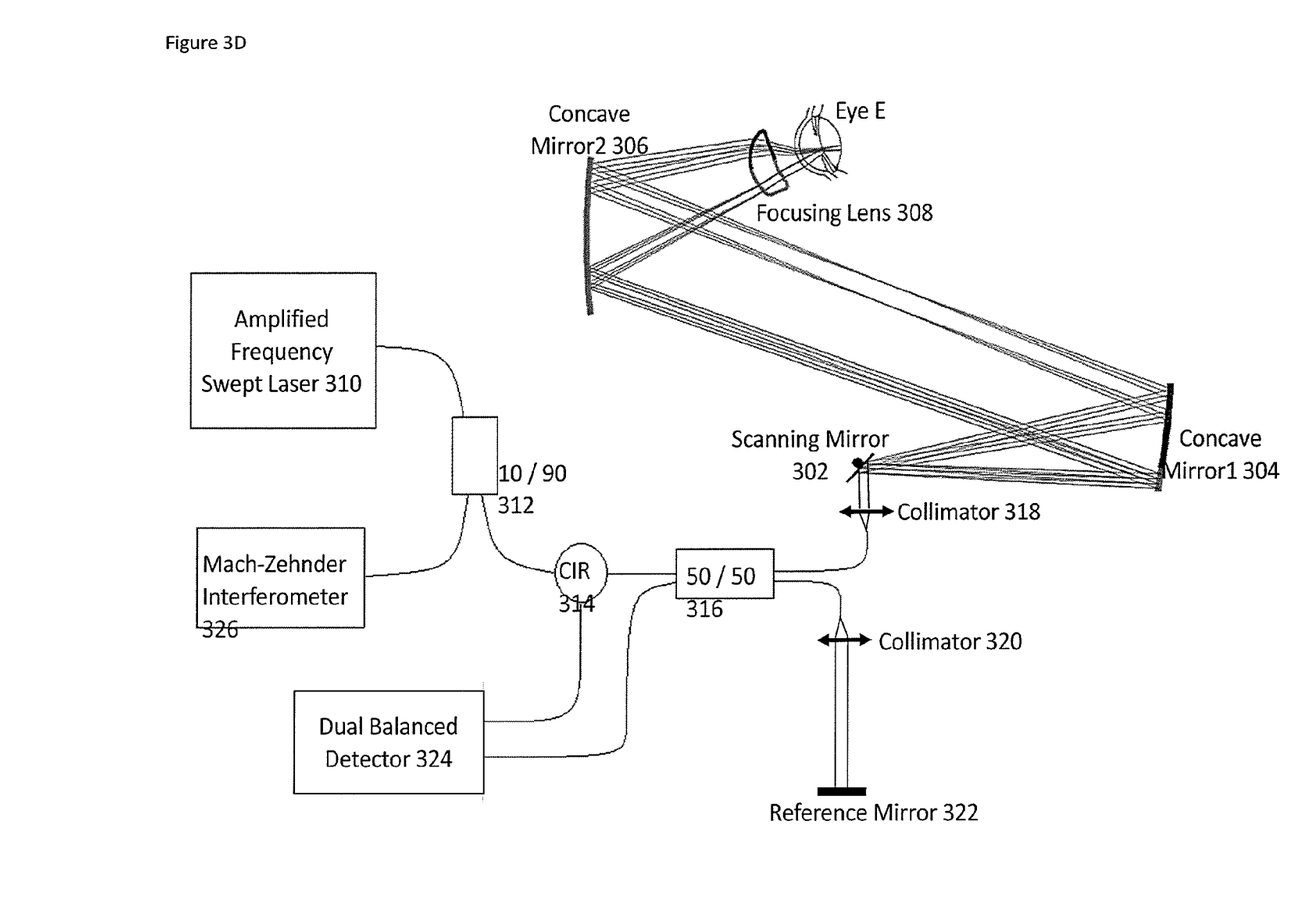
Figure 3E:
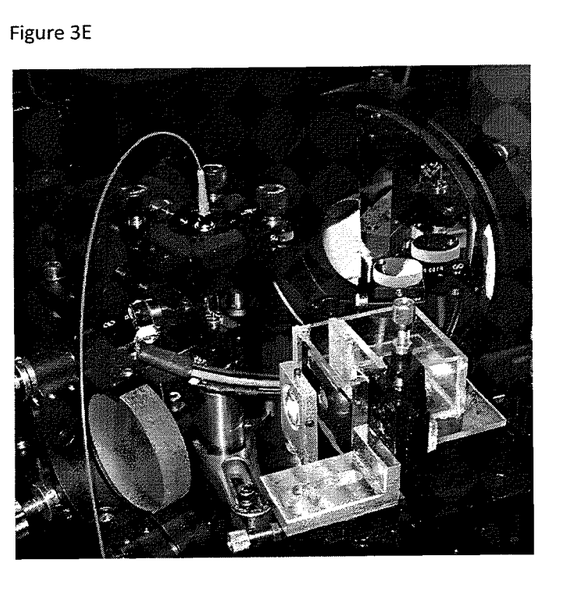
FIG. 3E is a photograph, that show a second design principle of the present invention.
Figure 3F:
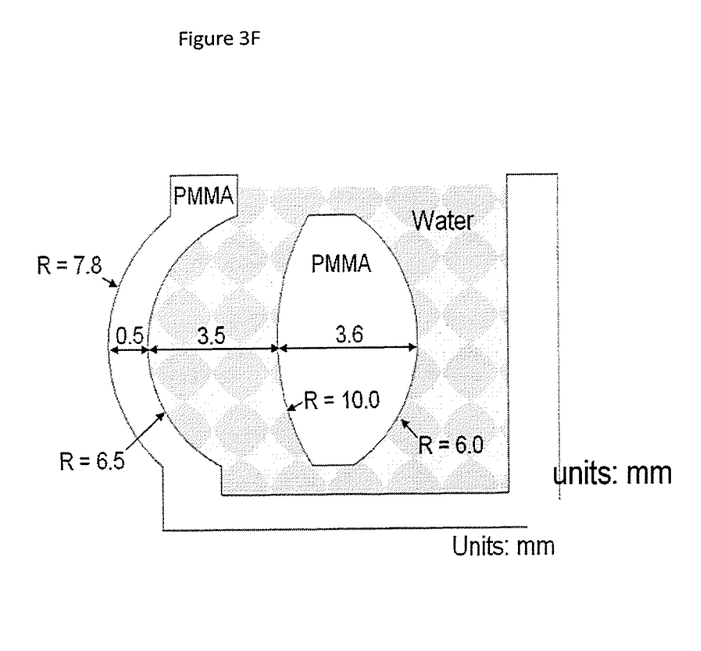

FIG. 3B shows a ray diagram of the asymmetric scanning system of the preferred embodiment. The optical elements include a scanning mirror 302, a first concave mirror 304, and a second concave mirror 306. FIG. 3C adds a focusing lens 308 and shows the position of the above elements relative to the eye E. As explained above, the focusing lens 308 includes two half lenses 308a, 308b glued or otherwise fastened together to achieve the two types of scanning noted above. The first concave mirror 304 is asymmetric and includes two components corresponding to the two half lenses; the second concave mirror 306 is symmetric. FIG. 3D shows the above and also optics including an amplified frequency swept laser 310, a 10/90 beamsplitter 312, a circulator 314, a 50/50 beamsplitter 316, collimators 318 and 320, a reference mirror 322, a dual balanced detector 324, and a Mach-Zehnder interferometer 326. FIGS. 3E and 3F are a photograph of a test system and a diagram of a test eye used in the system, respectively.

Two optical systems are used in the preferred embodiment. One is the asymmetric relay optics with one asymmetric concave mirror and symmetric concave mirror with different radii of curvatures. The other is the asymmetric focusing lens in front of the eye. These two systems are dependent each other to achieve what is needed; if the design of one of the two systems is changed, the other has to be redesigned as well.

Figure 4A:
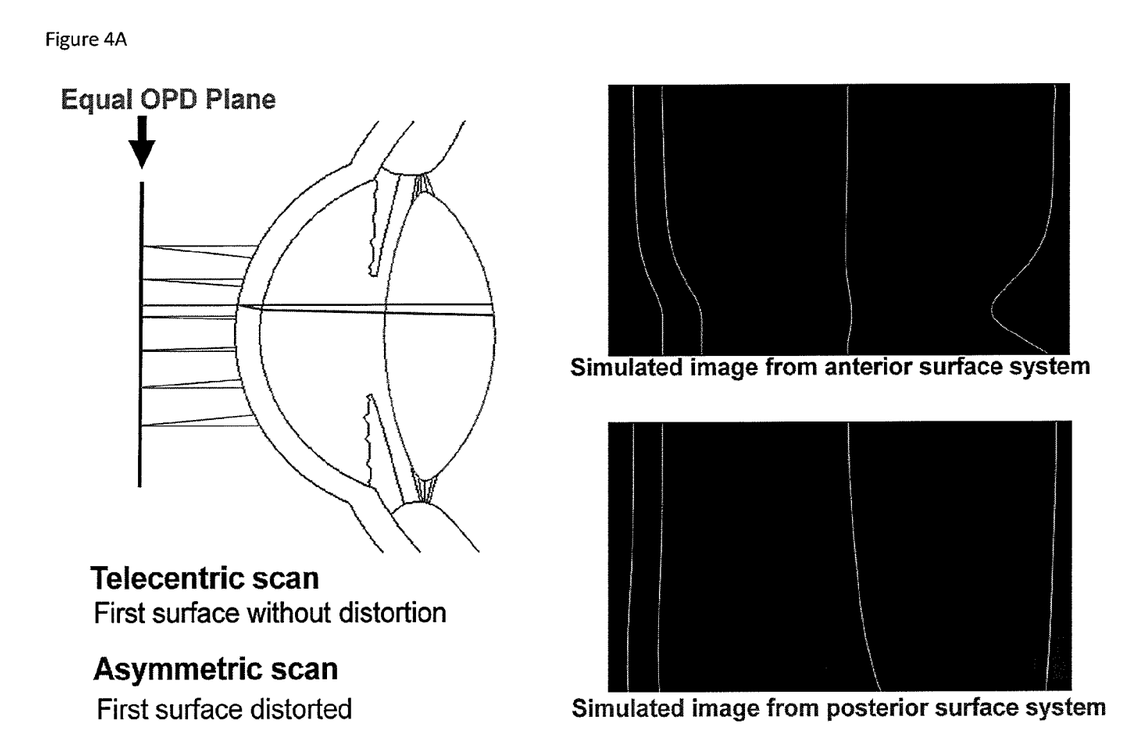
FIGS. 4A and 4B are diagrams that show image distortion.
Figure 4B:
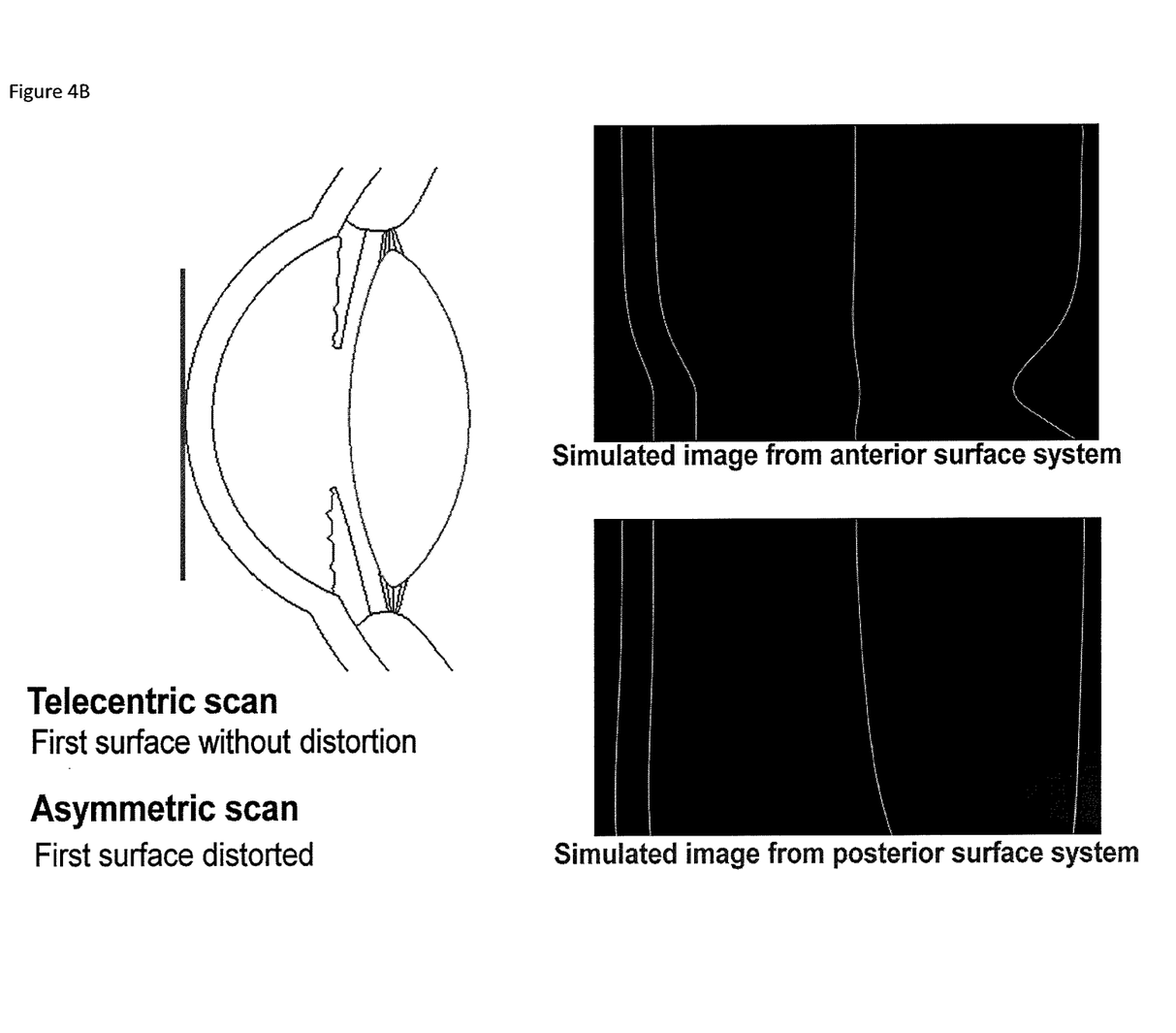

FIGS. 4A and 4B show image distortion in telemetric versus asymmetric scans. Owing to the nontelecentric nature of the present scanning method, large amounts of refractive distortion are expected in the images even for the first surface. The expected distortion was theoretically evaluated by optical ray tracing software (CodeV, Optical Research Associates). FIG. 4A shows the expected raw images from anterior and posterior lens surface scan geometries. Note that these images represent only half of the anterior segment. To correct for these distortions, a flat surface, placed at the same axial location as the first surface of the model eye, was imaged, as shown in FIG. 4B. The distortion obtained for the flat surface was then used as a reference to construct the true first surface. Subsequent surface distortions were then compensated by using ray tracing.

Figure 5:
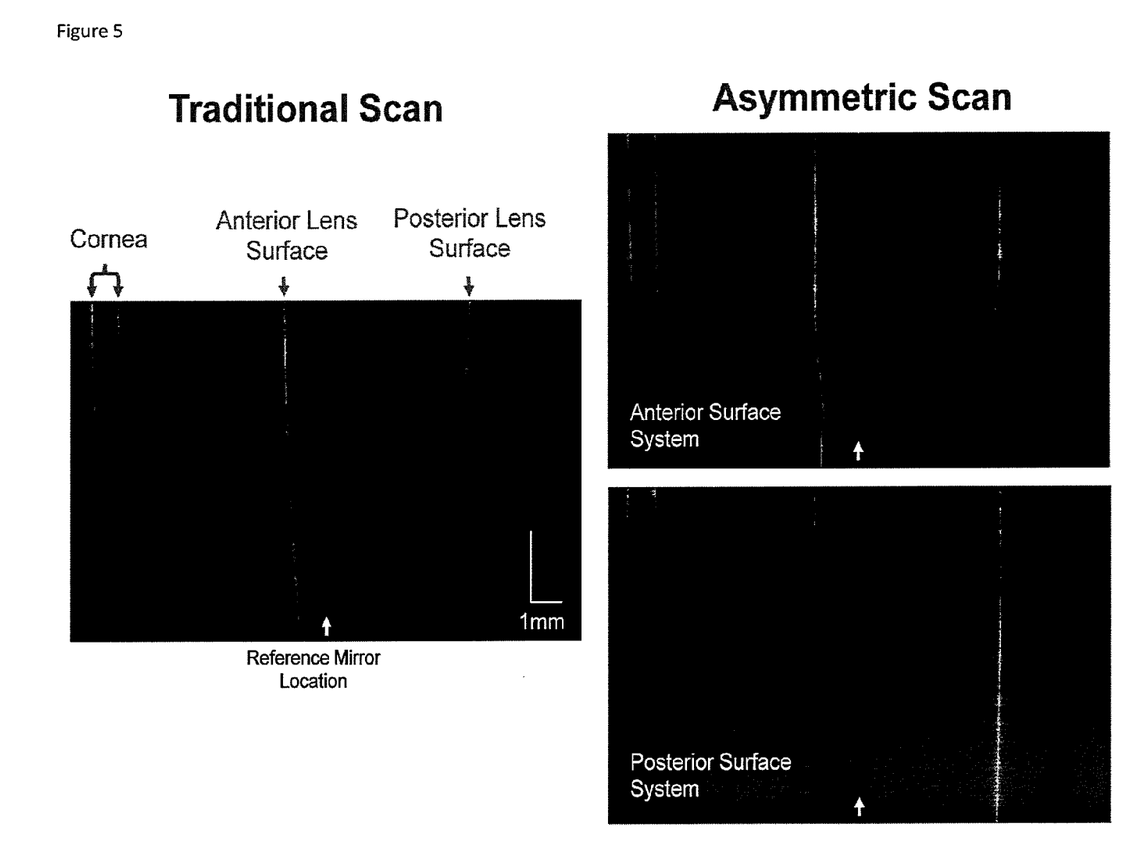
FIG. 5 is a set of scans that show imaging performance.
Figure 6:
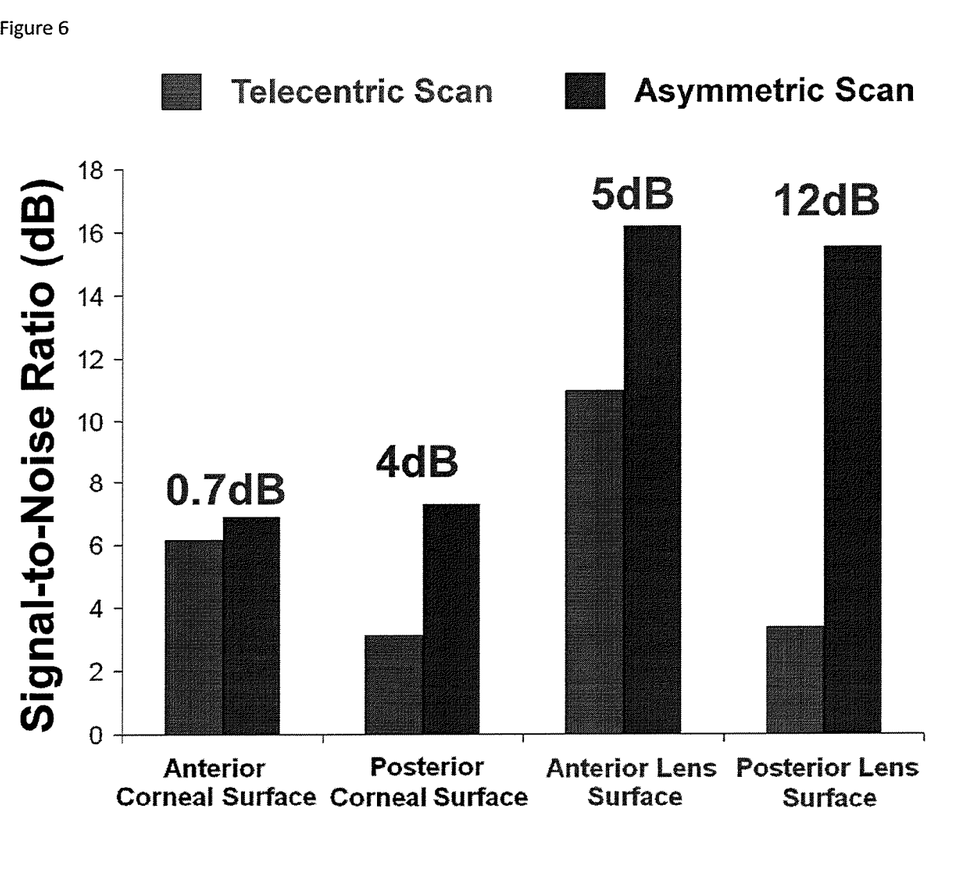
FIG. 6 is a graph that shows the improvement in signal-to-noise ratio.
Figure 7:
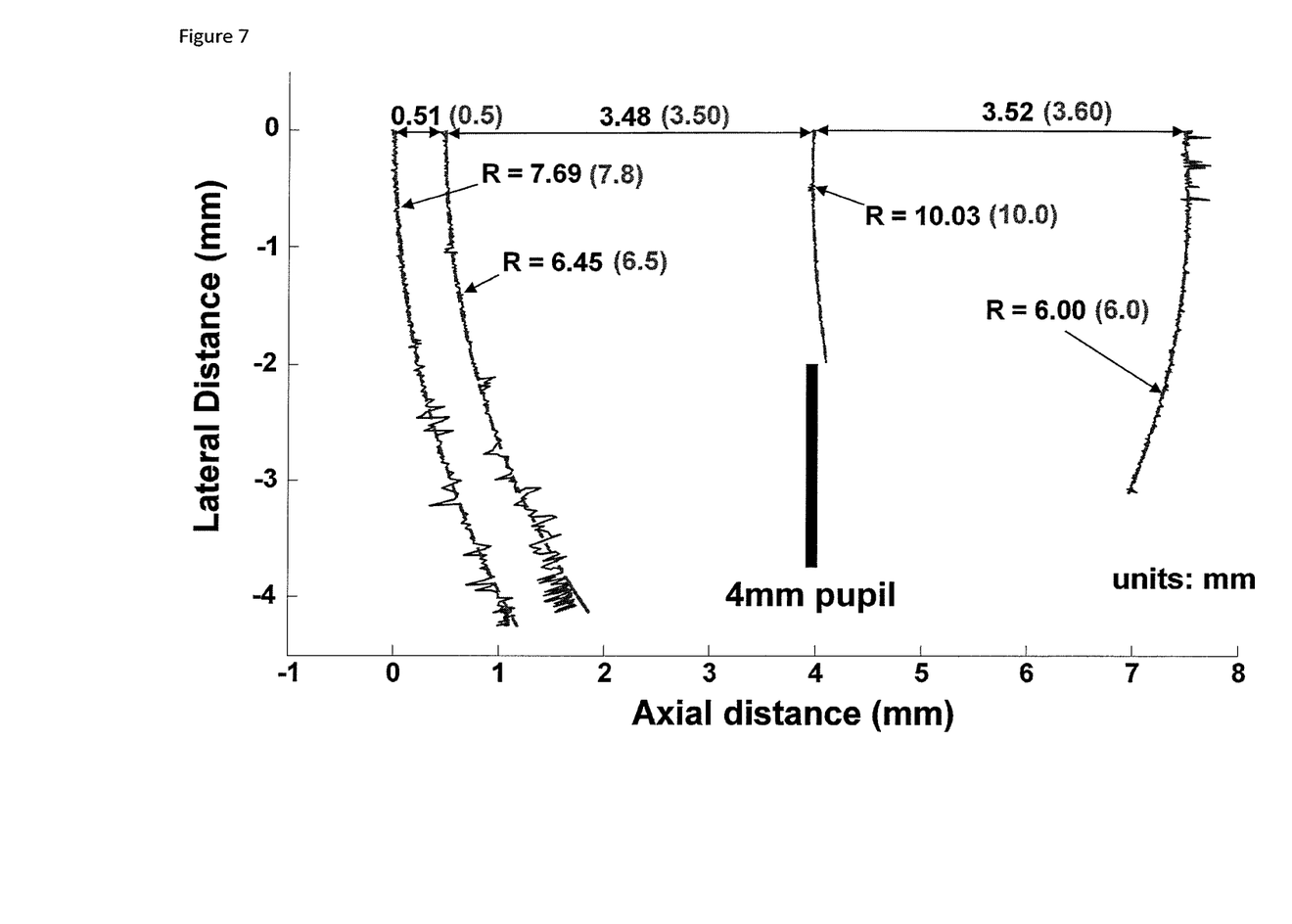
FIG. 7 is a graph that shows distortion-corrected surface profiles.

FIG. 5 shows imaging performance in traditional versus asymmetric scans. FIG. 6 shows the improvement in the signal-to-noise ratio. FIG. 7 shows distortion-corrected surface profiles.

More specifically, the images obtained by a swept source OCT system ($\lambda$=1300 nm, $\delta\lambda$=100 nm) for the model eye by using a conventional telecentric scan (FIG. 5, left) and the scanning system according to the preferred embodiment (FIG. 5, right) are shown. The distortion observed in FIG. 5 has a good agreement with the distortion theoretically predicted. Each image consists of 400 A scans. The SNR for each interface was obtained by dividing the peak amplitude corresponding to a particular interface by the average of a portion of the noise floor. The region used for averaging the noise floor was kept consistent for each A scan. The SNR values for each interface were then averaged over all A scans. An average SNR improvement of 5 and 12 dB was obtained for the anterior and posterior lens surfaces, respectively. For the posterior corneal surface SNR improvement of 4 dB was observed, while the SNR improvement for the anterior corneal surface was 0:7 dB. FIG. 7 shows the distortion-corrected surface profiles along with the fitted circular curves. The fitted values are nearly identical to the actual values with a relatively small discrepancy. These errors might arise because of slight tilt and decentration of the artificial cornea and lens in the model eye and the flat surface to be used as the reference.

From the above, the following may be concluded. The proposed scanning method significantly increases scan-depth and SNR. A larger diameter of the posterior surface of the lens is thus imaged without pupil dilation. Anterior segment OCT with the proposed scanning system can be a powerful tool for understanding the mechanism of accommodation and presbyopia.

While a preferred embodiment has been set forth in detail above, those skilled in the art who have reviewed the present disclosure will readily appreciate that other embodiments can be realized within the scope of the invention. For example, the specifics of the system shown in FIGS. 3A-3F can be varied in accordance with any desired optical techniques. Therefore the present invention should be construed as limited only by the appended claims.

We claim:

1. A scanning system for performing optical coherence tomography on a patient's eye, the scanning system comprising:
   a light source for emitting light;
   optics for causing the light from the light source to be incident on the eye's lens, the optics comprising:
      a first lens component for causing light to be normal on the anterior surface of the eye's lens; and
      a second lens component for causing the light to be normal on the posterior surface of the eye's lens; and
   a detector for detecting light reflected from the eye.

2. The scanning system of claim 1, wherein the first and second lens components are attached together.

3. The scanning system of claim 2, wherein the first and second lens components are glued together.

4. The scanning system of claim 1, further comprising a relay scanning system for scanning the light across the eye's lens.

5. The scanning system of claim 4, wherein the relay scanning system comprises a first concave mirror having two mirror components corresponding to the two lens components.

6. The scanning system of claim 5, wherein the relay scanning system further comprises a second concave mirror that is symmetric, wherein the first and second concave mirrors have different radii of curvature.

7. A method for performing optical coherence tomography on a patient's eye, the method comprising:
   (a) emitting light from a light source;
   (b) causing the light from the light source to be incident on the eye's lens such that a first part of the light is normal on the anterior surface of the eye's lens and a second part of the light is normal on the posterior surface of the eye's lens; and
   (c) detecting light reflected from the eye.

8. The method of claim 7, wherein step (b) is performed using optics for causing the light from the light source to be incident on the eye's lens, the optics comprising:
   a first lens component for causing light to be normal on the anterior surface of the eye's lens; and
   a second lens component for causing the light to be normal on the posterior surface of the eye's lens.

9. The method of claim 8, wherein the first and second lens components are attached together.

10. The method of claim 9, wherein the first and second lens components are glued together.

11. The method of claim 7, further comprising using a relay scanning system for scanning the light across the eye's lens.

12. The method of claim 11, wherein the relay scanning system comprises a first concave mirror having two mirror components corresponding to the two lens components.

13. The method of claim 12, wherein the relay scanning system further comprises a second concave mirror that is symmetric, wherein the first and second concave mirrors have different radii of curvature.

* * * * *